US009144499B2

(12) United States Patent
Lizak et al.

(10) Patent No.: US 9,144,499 B2
(45) Date of Patent: Sep. 29, 2015

(54) LOW PROFILE MOBILE/FIXED PROSTHETIC KNEE SYSTEMS

(71) Applicant: DEPUY (IRELAND), Cork (IE)

(72) Inventors: John F Lizak, Somerset, MA (US); Stephen A Hazebrouck, Winona Lake, IN (US)

(73) Assignee: DEPUY (IRELAND), Cork (IE)

( * ) Notice: Subject to any disclaimer, the term of this patent is extended or adjusted under 35 U.S.C. 154(b) by 37 days.

(21) Appl. No.: 14/109,037

(22) Filed: Dec. 17, 2013

(65) Prior Publication Data
US 2015/0164648 A1 Jun. 18, 2015

(51) Int. Cl.
A61F 2/38 (2006.01)

(52) U.S. Cl.
CPC ............... *A61F 2/3868* (2013.01); *A61F 2/389* (2013.01)

(58) Field of Classification Search
CPC . A61F 2/38; A61F 2/3868; A61F 2220/0025; A61F 2/389
See application file for complete search history.

(56) References Cited

U.S. PATENT DOCUMENTS

| 5,282,868 | A | 2/1994 | Bahler |
| 5,358,530 | A | 10/1994 | Hodorek |
| 5,728,748 | A | 3/1998 | Sun |
| 5,871,541 | A | 2/1999 | Gerber |
| 5,879,400 | A | 3/1999 | Merrill |
| 6,017,975 | A | 1/2000 | Saum |
| 6,190,415 | B1 | 2/2001 | Cooke |
| 6,228,900 | B1 | 5/2001 | Shen |
| 6,242,507 | B1 | 6/2001 | Saum |
| 6,245,276 | B1 | 6/2001 | McNulty |
| 6,281,264 | B1 | 8/2001 | Salovey |
| 6,316,158 | B1 | 11/2001 | Saum |
| 6,342,075 | B1 | 1/2002 | MacArthur |
| 8,187,335 | B2 | 5/2012 | Wyss |
| 8,192,498 | B2 | 6/2012 | Wagner |
| 8,206,451 | B2 | 6/2012 | Wyss |
| 8,236,061 | B2 | 8/2012 | Heldreth |
| 8,658,710 | B2 | 2/2014 | McKellop |
| 2001/0047211 | A1 | 11/2001 | Leclercq |
| 2003/0212161 | A1 | 11/2003 | McKellop |
| 2006/0190086 | A1 | 8/2006 | Clemow |
| 2008/0091273 | A1 | 4/2008 | Hazebrouck |
| 2009/0326667 | A1 | 12/2009 | Williams |
| 2010/0016980 | A1 | 1/2010 | Donno |
| 2010/0191342 | A1 | 7/2010 | Byrd |
| 2011/0190898 | A1 | 8/2011 | Lenz |

FOREIGN PATENT DOCUMENTS

EP 0672397 A1 9/1995

OTHER PUBLICATIONS

PCT International Search Report and Written Opinion for Corresponding International Application No. PCT/US2014/070269 Dated March 17, 2015, 4 Pages.

*Primary Examiner* — Jason-Dennis Stewart

(57) ABSTRACT

A knee prosthesis system has a tibial component with frame with medial and lateral openings to receive the medial and lateral bearing components. The bearing components have distal surfaces that are exposed when assembled with the frame and pegs extending distally from the distal surfaces. The system optionally includes a tibial base plate with elongated curved receptacles to receive the pegs and allow the frame and bearing component assembly to rotate when mounted on the base plate. Different thicknesses of bearing components can be selectively locked onto the frame. Different sizes of tibial components have commonly sized, shaped and positioned elements so that multiple sizes of tibial components can be mounted on the same prepared tibial surface.

15 Claims, 10 Drawing Sheets

US 9,144,499 B2

LOW PROFILE MOBILE/FIXED PROSTHETIC KNEE SYSTEMS

TECHNICAL FIELD

The present disclosure relates generally to an orthopaedic prosthesis, and more particularly to a knee prosthesis. Specifically, the present disclosure relates to the tibial and bearing components of a knee prosthesis system.

BACKGROUND

Movement (e.g., flexion and extension) of the natural human knee involves movements of the femur and the tibia. Specifically, during flexion and extension, the distal end of the femur and the proximal end of the tibia articulate relative to one another through a series of complex movements. Damage (e.g., trauma) or disease can deteriorate the bones, articular cartilage, and ligaments of the knee, which can ultimately affect the ability of the natural knee to function in such a manner. As a result, knee prostheses have been developed and implanted into surgically prepared ends of the femur and tibia.

A typical knee prosthesis for a total knee replacement includes, for example, a tibial component or tibial tray coupled to the patient's tibia, a femoral component coupled to the patient's femur, and a bearing component (or tibial insert) positioned between the tibial tray and the femoral component and including a bearing surface to accommodate the condyles of the femoral component. In some situations, it may be desirable that the tibial insert rotate relative to the tibial tray. Such rotation more closely replicates the motion of the patient's natural anatomy. In other cases, however, it may be desirable to prevent the tibial insert from rotating relative to the tibial tray. For example, various ligaments that support the knee may be compromised or damaged. In such a case, rotation of the tibial insert relative to the tibial tray may create an unstable knee. As such, a surgeon will decide on a case-by-case basis whether to use a rotating or non-rotating (fixed) tibial assembly.

Although all-polymer tibial components are available, commonly used tibial trays and tibial bearing components generally are designed so that the bearing component, whether fixed or rotating, is supported on a solid metal tray surface. The thickness of such an assembly of a tibial tray and bearing will require the removal of a certain amount of bone from the proximal tibia. Since preservation of healthy native bone is desirable in total knee replacement surgery, it is desirable to minimize the amount of bone required to be removed to accommodate the thickness of the tibial component. On the other hand, maintaining adequate properties of the tibial bearing requires that the bearing have some minimal thickness. Accordingly, it is desirable to provide a knee prosthesis system where the thickness of the tibial implant component is decreased while maintaining adequate thickness of the polymer bearing component.

In addition, it is desirable to provide a knee prosthesis system that allows for intraoperative flexibility in selecting the appropriate size and type (fixed or mobile) of components after the bone surface has been prepared.

SUMMARY

According to one aspect, the present invention provides a knee prosthesis system comprising a femoral component and a tibial component. The femoral component has medial and lateral condyles with curved articulating surfaces. The tibial component comprises a frame, a first medial bearing component and a separate first lateral bearing component. The frame has an anterior portion, a posterior portion, a medial portion extending between the anterior portion and the posterior portion, a lateral portion extending between the anterior portion and the posterior portion, a central portion extending between the anterior portion and the posterior portion and a stem extending distally from the central portion. The stem has a central longitudinal axis and an outer surface tapering distally toward the central longitudinal axis. The anterior, posterior, medial, lateral and central portions define spaced first medial and first lateral openings. The first medial opening extends from the medial portion of the first frame to the central portion of the first frame and the first lateral opening extends from the lateral portion of the first frame to the central portion of the first frame. The anterior, posterior, medial and central portions of the frame have side walls facing the medial opening and side walls facing the lateral opening. The first medial bearing component includes a proximal bearing surface, a distal surface, a peg extending distally from the distal surface and side walls extending between the proximal bearing surface and distal surface; the proximal bearing surface is sized and shaped to articulate with the curved articulating surface of the medial condyle of the femoral component. The first lateral bearing component includes a proximal bearing surface, a distal surface, a peg extending distally from the distal surface and side walls extending between the proximal bearing surface and distal surface; the proximal bearing surface is sized and shaped to articulate with the curved articulating surface of the lateral condyle of the femoral component. The first medial bearing component is sized and shaped to fit within the first medial opening in the first frame with the side walls of the first medial bearing component juxtaposed with the side walls of the first frame facing the first medial opening. The first lateral bearing component is sized and shaped to fit within the first lateral opening in the first frame with the side walls of the first lateral bearing component juxtaposed with the side walls of the first frame facing the first lateral opening. The side walls of the first medial bearing component, first lateral bearing component and first frame having complementary locking members to selectively lock the first medial bearing component in the first medial opening and the first lateral bearing component in the first lateral opening. The first frame and first medial bearing component and first lateral bearing component can be assembled with the first medial bearing component received within the first medial opening so that the side walls of the first medial bearing component and side walls of the first frame surrounding the medial opening lock together to selectively fix the first medial bearing component to the first frame and so that the side walls of the first lateral bearing component and side walls of the first frame surrounding the first lateral opening lock together to selectively fix the first lateral bearing component to the first frame.

In a more particular embodiment, multiple medial and lateral bearing components are provided having different thicknesses. In this embodiment, the first medial bearing component has a minimum thickness between the proximal bearing surface and the distal surface and the first lateral bearing component has a minimum thickness between the proximal bearing surface and the distal surface. A second medial bearing component includes a proximal bearing surface, a distal surface, a peg extending distally from the distal surface and side walls extending between the proximal bearing surface and distal surface; the proximal bearing surface is sized and shaped to articulate with the curved articulating surface of the medial condyle of the femoral component. The second medial bearing component has a minimum thickness greater than the minimum thickness of the first medial bearing component. A second lateral bearing component includes a proximal bearing surface, a distal surface, a peg extending distally from the distal surface and side walls extending between the proximal bearing surface and distal surface; the proximal bearing surface is sized and shaped to articulate with the curved articulating surface of the lateral condyle of the femoral component. The second lateral bearing component has a minimum thickness greater than the minimum thickness of the first lateral bearing component. The side walls of the second medial bearing component and second lateral bearing component have locking members complementary to the locking members of the first frame to selectively lock the second medial bearing component in the first medial opening and the second lateral bearing component in the first lateral opening. The first frame and second medial bearing component and second lateral bearing component can be assembled with the second medial bearing component received within the medial opening so that the side walls of the second medial bearing component and side walls of the first frame surrounding the medial opening lock together to selectively fix the second medial bearing component to the first frame and so that the side walls of the second lateral bearing component and side walls of the first frame surrounding the lateral opening lock together to selectively fix the second lateral bearing component to the first frame.

More particularly, various combinations of bearings may be used with the system described in the preceding paragraph. For example, the first frame could be assembled with the first medial bearing component locked in place in the first medial opening and the second lateral bearing component locked in place in the first lateral opening. Alternatively, the first frame could be assembled with the second medial bearing component locked in place in the first medial opening and the first lateral bearing component locked in place in the first lateral opening. Alternatively, the first frame could be assembled with the first medial bearing component locked in place in the first medial opening and the first lateral bearing component locked in place in the first lateral opening. In addition, the first frame could be assembled with the second medial bearing component locked in place in the first medial opening and the second lateral bearing component locked in place in the first lateral opening. Additional variations are possible if additional bearing components are provided.

In another more particular embodiment, the knee prosthesis system allows the surgeon to opt to use a mobile bearing design. In this embodiment, a tibial base plate is provided. The tibial base plate includes a proximal surface and a distal surface, a stem extending distally from the distal surface, a curved medial keel extending distally from the distal surface, a curved lateral keel extending distally from the distal surface, a curved medial receptacle in the proximal surface corresponding in shape and position with and extending into the curved medial keel, a curved lateral receptacle in the proximal surface corresponding in shape and position with and extending into the curved lateral keel and a central receptacle in the proximal surface extending into the stem. An assembly of the first frame and the first medial bearing component and first lateral bearing component is rotatably mountable on the tibial base plate with the stem of the first frame received in the central receptacle and the peg of the medial bearing component received in the curved medial receptacle and the peg of the lateral bearing component received in the curved lateral receptacle. The pegs and curved medial receptacle and curved lateral receptacle are sized and shaped so that the pegs of the first medial bearing component and first lateral bearing component can travel along curved paths as the first frame and first medial bearing component and first lateral bearing component rotate on the tibial base plate.

In another more particular aspect, the first frame has a proximal surface and a distal surface. When assembled with the first frame, the pegs of the first medial and first lateral bearing components extend beyond the level of the distal surface of the frame. In this embodiment, the distal surfaces of the first medial and lateral bearing components may be planar so that when assembled with the first frame, the distal surfaces of the first medial and lateral bearing components also extend distally beyond the level of the distal surface of the first frame. In a particular embodiment, the distal surface of the first frame lies in a distal plane and includes surfaces of the anterior portion, posterior portion, medial portion and central portion of the first frame, and the stem is the only part of the frame that extends beyond this distal plane.

In another particular embodiment of the embodiment described in the preceding paragraph, the knee prosthesis may further comprise a tibial base plate. The tibial base plate may include a proximal surface, a distal surface, a stem extending distally from the distal surface, a curved medial keel extending distally from the distal surface, a curved lateral keel extending distally from the distal surface, a curved medial receptacle in the proximal surface corresponding in shape and position with and extending into the curved medial keel, a curved lateral receptacle in the proximal surface corresponding in shape and position with and extending into the curved lateral keel and a central receptacle in the proximal surface extending into the stem. An assembly of the first frame and the first medial bearing component and first lateral bearing component is rotatably mountable on this tibial base plate with the stem of the first frame received in the central receptacle, the peg of the first medial bearing component received in the curved medial receptacle, the peg of the first lateral bearing component received in the curved lateral receptacle, the distal surface of the first medial bearing component contacting the proximal surface of the tibial base plate, the distal surface of the first lateral bearing component contacting the proximal surface of the tibial base plate, and the plane of the distal surface of the tibial frame is spaced from the proximal surface of the tibial base plate. In this embodiment, the pegs and curved medial receptacle and curved lateral receptacle are sized and shaped so that the pegs of the first medial bearing component and first lateral bearing component can travel along curved paths as the first frame and first medial bearing component and first lateral bearing component rotate on the tibial base plate.

In another particular embodiment, the knee prosthesis system includes a second tibial component comprising a second frame, a second medial bearing component and a second lateral bearing component. Like the first frame, the second frame has an anterior portion, a posterior portion, a medial portion extending between the anterior portion and the posterior portion, a lateral portion extending between the anterior portion and the posterior portion, a central portion extending from the anterior portion to the posterior portion, and a stem extending distally from the central portion. The stem has a central longitudinal axis and an outer surface tapering distally toward the central longitudinal axis. The anterior, posterior, medial, lateral and central portions define spaced medial and lateral openings. The medial opening extends from the medial portion of the second frame to the central portion of the frame and the lateral opening extends from the lateral portion of the second frame to the central portion of the second frame. The anterior portion, medial portion and central portion having side walls facing the medial opening and side walls facing the lateral opening. The first tibial component has a maximum medial-lateral dimension at the medial and lateral portions of the frame and a maximum central anterior-posterior dimension along the central portion. The second tibial component has a maximum medial-lateral dimension at the medial and lateral portions of the frame and a maximum central anterior-posterior dimension along the central portion. The maximum medial-lateral dimension of the second tibial component is greater than the maximum medial-lateral dimension of the first tibial component. The second medial bearing component includes a proximal bearing surface, a distal surface, a peg extending distally from the distal surface and side walls extending between the proximal bearing surface and distal surface. The proximal bearing surface is sized and shaped to articulate with the curved articulating surface of the medial condyle of the second femoral component. The second lateral bearing component includes a proximal bearing surface, a distal surface, a peg extending distally from the distal surface and side walls extending between the proximal bearing surface and distal surface, the proximal bearing surface being sized and shaped to articulate with the curved articulating surface of the lateral condyle of the second femoral component. The second medial bearing component is sized and shaped to fit within the medial opening in the second frame with the side walls of the second medial bearing component juxtaposed with the side walls of the frame facing the medial opening. The second lateral bearing component is sized and shaped to fit within the lateral opening in the second frame with the side walls of the lateral bearing component juxtaposed with the side walls of the second frame facing the lateral opening. The side walls of the second medial bearing component, second lateral bearing component and second frame have complementary locking members to selectively lock the second medial bearing component in the medial opening and the second lateral bearing component in the lateral opening. The second frame and second medial and second lateral bearing components can be assembled with the second medial bearing component received within the second medial opening so that the side walls of the second medial bearing component and side walls of the second frame surrounding the second medial opening lock together to selectively fix the second medial bearing component to the second frame and so that the side walls of the second lateral bearing component and side walls of the second frame surrounding the second lateral opening lock together to selectively fix the second lateral bearing component to the second frame.

In the embodiment described in the preceding paragraph, the peg of the first medial bearing component may have the same size and shape as the peg of the second medial bearing component and the peg of the first lateral bearing member may have the same size and shape as the peg of the second lateral bearing member. In this embodiment, the distance from the central longitudinal axis of the stem of the first frame to a point on the peg of the first medial bearing component is the same as the distance from the central longitudinal axis of the stem of the second frame to a corresponding point on the peg of the second medial bearing component when the first medial bearing component is assembled with the first frame and the second medial bearing component is assembled with the second frame. In addition, in this embodiment the distance from the central longitudinal axis of the stem of the first frame to a point on the peg of the first lateral bearing component is the same as the distance from the central longitudinal axis of the stem of the second frame to a corresponding point on the peg of the second lateral bearing component when the first lateral bearing component is assembled with the first frame and the second lateral bearing component is assembled with the second frame.

In the embodiment described in the preceding paragraph, the system may further comprise a pair of differently sized tibial base plates that may be used to create a mobile bearing prosthesis. Each tibial base plate in this embodiment includes a proximal surface, a distal surface, a stem extending distally from the distal surface, a curved medial keel extending distally from the distal surface, a curved lateral keel extending distally from the distal surface, a curved medial receptacle in the proximal surface corresponding in shape and position with and extending into the curved medial keel, a curved lateral receptacle in the proximal surface corresponding in shape and position with and extending into the curved lateral keel and a central receptacle in the proximal surface extending into the stem. In this embodiment, an assembly of the first frame and the first medial bearing component and first lateral bearing component is rotatably mountable on each tibial base plate with the stem of the first frame received in the central receptacle of the tibial base plate and the peg of the medial bearing component received in the curved medial receptacle and the peg of the lateral bearing component received in the curved lateral receptacle. The pegs and each curved medial receptacle and curved lateral receptacle are sized and shaped so that the pegs of the first medial bearing component and first lateral bearing component can travel along curved paths as the first frame and first medial bearing component and first lateral bearing component rotate on each tibial base plate. The distance from the central longitudinal axis of the stem of the first tibial base plate to a point on the medial keel of the first tibial base plate is the same as the distance from the central longitudinal axis of the stem of the second tibial base plate to a corresponding point on the medial keel of the second tibial base plate. In addition, the distance from the central longitudinal axis of the stem of the first tibial base plate to a point on the lateral keel of the first tibial base plate is the same as the distance from the central longitudinal axis of the stem of the second tibial base plate to a corresponding point on the lateral keel of the second tibial base plate. In this embodiment, the first tibial base plate may have a maximum medial-lateral dimension and the second tibial base plate may have a greater maximum medial-lateral dimension.

BRIEF DESCRIPTION OF THE DRAWINGS

The detailed description particularly refers to the following figures, in which.

DETAILED DESCRIPTION OF THE DRAWINGS

Figure 1:
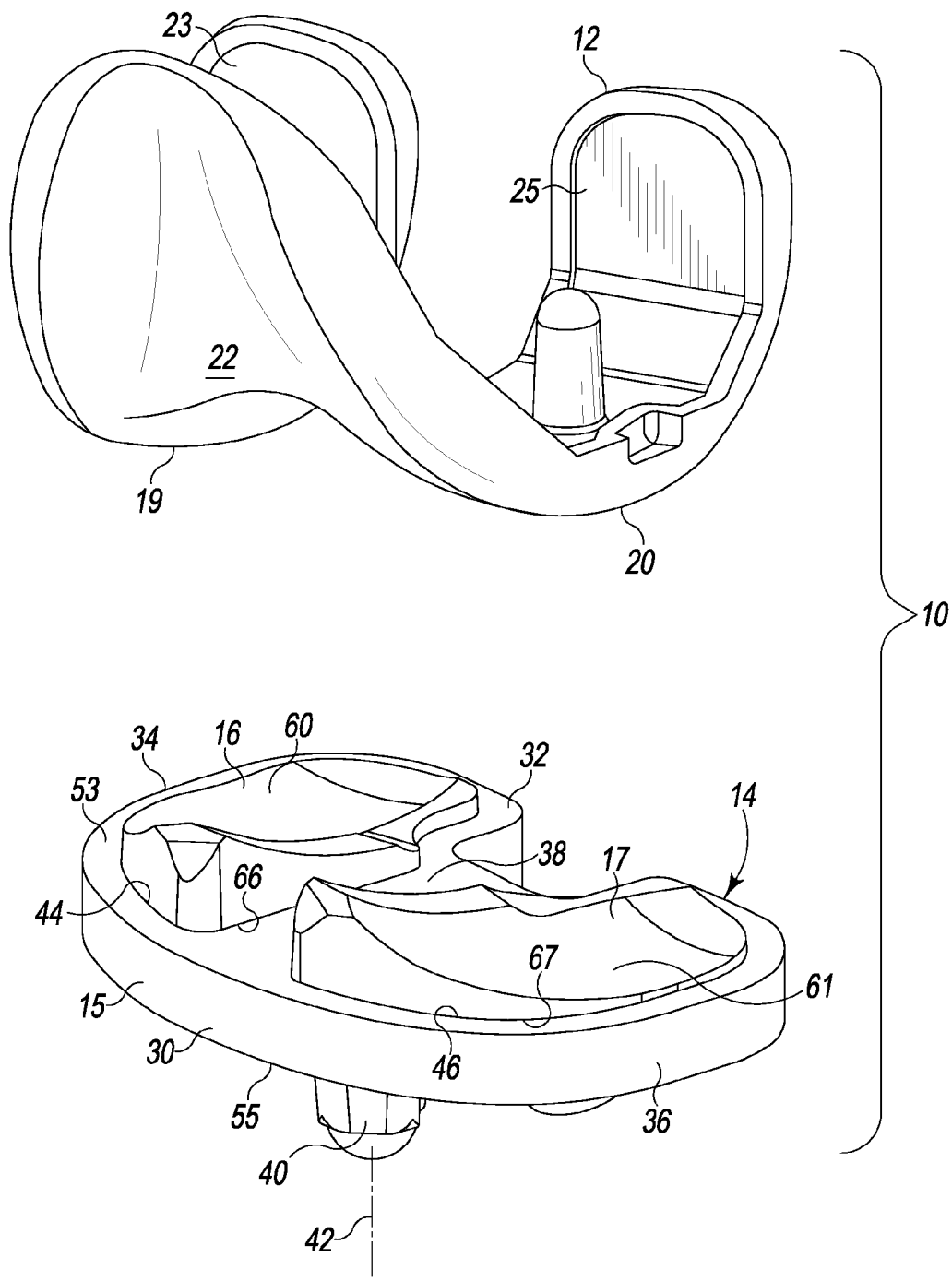
FIG. 1 is a perspective view of a fixed bearing knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, proximal, distal, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, there is shown a knee prosthesis 10. The knee prosthesis 10 includes a femoral component 12 and a tibial component 14. As described in more detail below, the tibial component 14 comprises an assembly of a frame 15, a medial bearing 16 and a lateral bearing 17. The knee prosthesis 10 of FIG. 1 is a fixed bearing knee prosthesis, meaning that no relative movement is intended to occur between the tibia and the bearings 16, 17.

Figure 2:
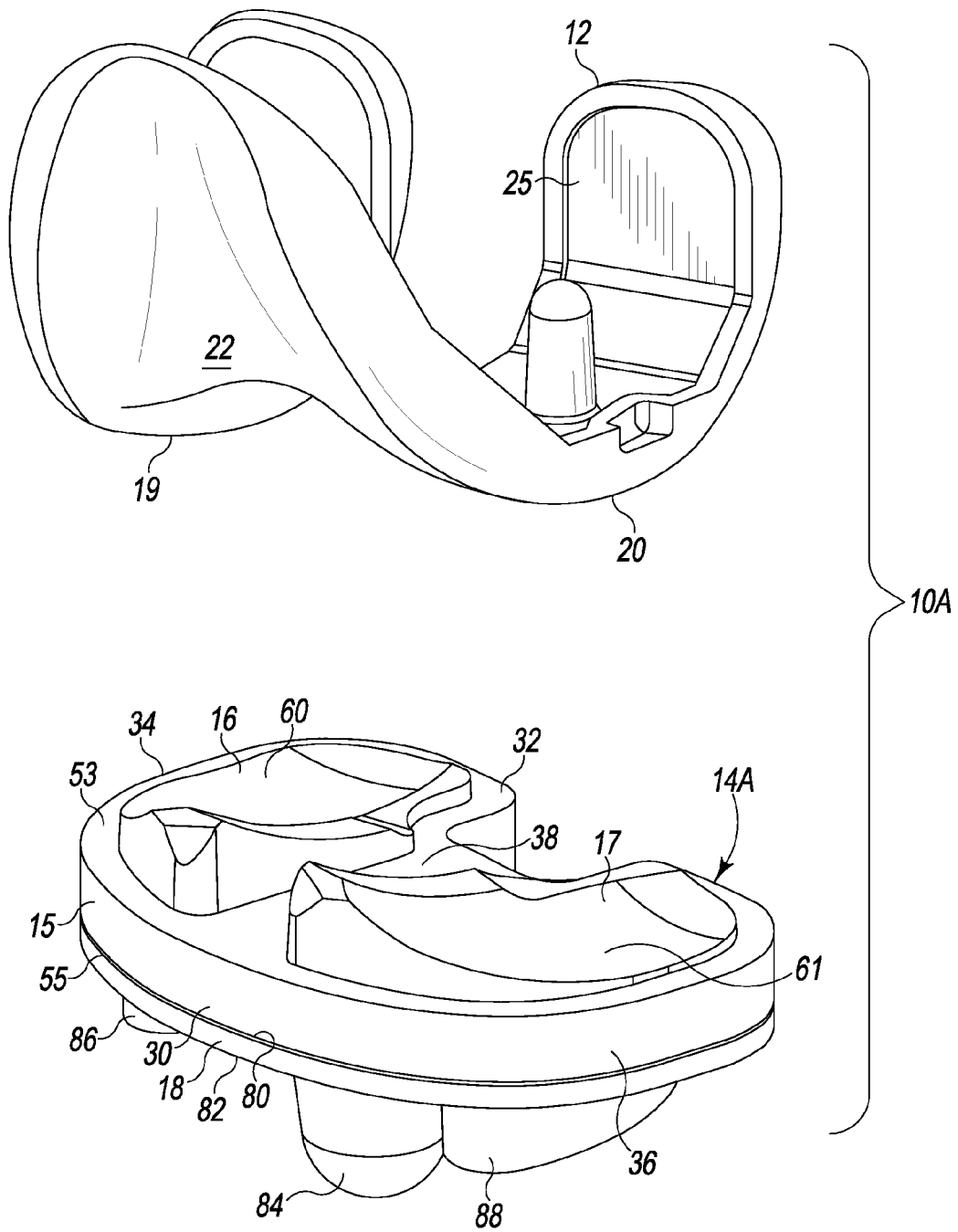
FIG. 2 is a perspective view of a mobile-bearing knee prosthesis utilizing the fixed bearing knee prosthesis of FIG. 1.
Figure 3:
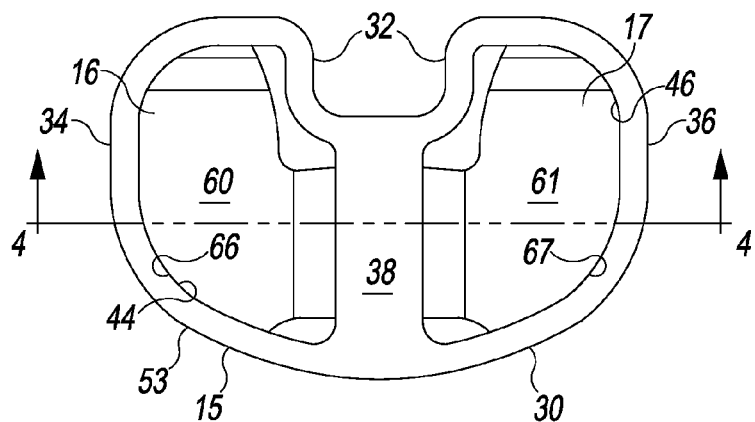
FIG. 3 is a top view of the tibial component of the mobile-bearing knee prosthesis of FIG. 2.

A mobile bearing knee prostheses is shown in FIG. 2 at 10A. In the mobile bearing design, the femoral component 12 may be the same as that illustrated in the fixed bearing design of FIG. 1. Moreover, the tibial frame 15, medial bearing 16 and lateral bearing 17 may be the same as those illustrated in the fixed bearing design of FIG. 1. The mobile bearing design of the FIG. 2 embodiment differs from the fixed bearing design of FIG. 1 in that the tibial component 14A of FIG. 2 also includes a tibial base plate 18, described in more detail below.

The illustrated femoral component 12 includes two condylar articulation surfaces: a medial condyle articulation surface 19 and a lateral condyle articulation surface 20. The femoral component 12 is configured to be implanted into a surgically prepared end of the patient's femur (not shown), and is configured to emulate the configuration of the patient's natural femoral condyles. As such, the lateral condyle surface 20 and the medial condyle surface 19 are configured (e.g., curved) in a manner which mimics the condyles of the natural femur. The lateral condyle surface 20 and the medial condyle surface 19 are spaced apart from one another thereby defining an intercondylar articulation surface 22 there between. The intercondylar articulation surface 22 defines a patella groove shaped to receive and bear against a patella implant component (not shown).

The femoral component 12 also includes bone-engaging surfaces 23, 25 opposite the articulation surfaces 19, 20. Some or all of the bone-engaging surfaces 23, 25 may comprise porous metal (as described below) conducive to bony ingrowth. Alternatively, in the embodiment of FIGS. 1-2, the bone-engaging surfaces of the femoral component 12 may include cement pockets to facilitate cementing the component to the bone.

The femoral component 12 of FIG. 1 is a cruciate retaining component, although it should be understood that the principles of the present invention are applicable to cruciate substituting prosthetic knee systems as well.

The femoral component 12 may include features of standard, commercially available implants, such as those available from DePuy Orthopaedics, Inc., Warsaw, Ind. (and its affiliates), as well as those available from other suppliers of prosthetic knee systems. The femoral component 12 may also include features described in the following United States patents and application, the disclosures of which are incorporated by reference herein in their entireties: "Orthopaedic Knee Prosthesis Having Controlled Condylar Curvature," U.S. Pat. No. 823,606; "Posterior Cruciate-Retaining Orthopaedic Knee Prosthesis Having Controlled Condylar Curvature," U.S. Pat. No. 8,192,498; "Orthopaedic Femoral Component Having Controlled Condylar Curvature," Ser. No. 12/165,579; "Posterior Stabilized Orthopaedic Prosthesis," U.S. Pat. No. 8,206,451; and "Posterior Stabilized Orthopaedic Knee Prosthesis Having Controlled Condylar Curvature," U.S. Pat. No. 8,187,335.

The articulation surfaces of the femoral component 12 may be constructed from a biocompatible metal, such as stainless steel, titanium, cobalt chrome alloy or titanium alloy, although other materials, such as ceramic or a polymer (such as polyetherether ketone or PEEK, for example), may also be used. Commonly used alloys include titanium alloy Ti-6Al-4V.

Turning now to the frame 15 of the tibial component 14, 14A, the frame 15 includes an anterior portion 30, a posterior portion 32, a medial portion 34 extending between the anterior portion 30 and the posterior portion 32, a lateral portion 36 extending between the anterior portion 30 and the posterior portion 32, a central portion 38 extending between the anterior portion 30 and the posterior portion 32 and a stem 40 extending distally from the central portion 38. The stem has a central longitudinal axis 42 and an outer surface tapering distally toward the central longitudinal axis.

The anterior portion 30, posterior portion 32, medial portion 34, lateral portion 36 and central portion 38 of the frame 15 define spaced medial and lateral openings 44, 46. The medial opening 44 extends from the medial portion 34 of the frame 15 to the central portion 38 of the frame 15. The lateral opening 46 extends from the lateral portion 36 of the frame 15 to the portion 38 of the frame 15. The medial and lateral openings 44, 46 define through-holes surrounded by portions of the frame; nothing extends across the openings 44, 46 in either a medial-lateral or anterior-posterior direction.

Figure 4:
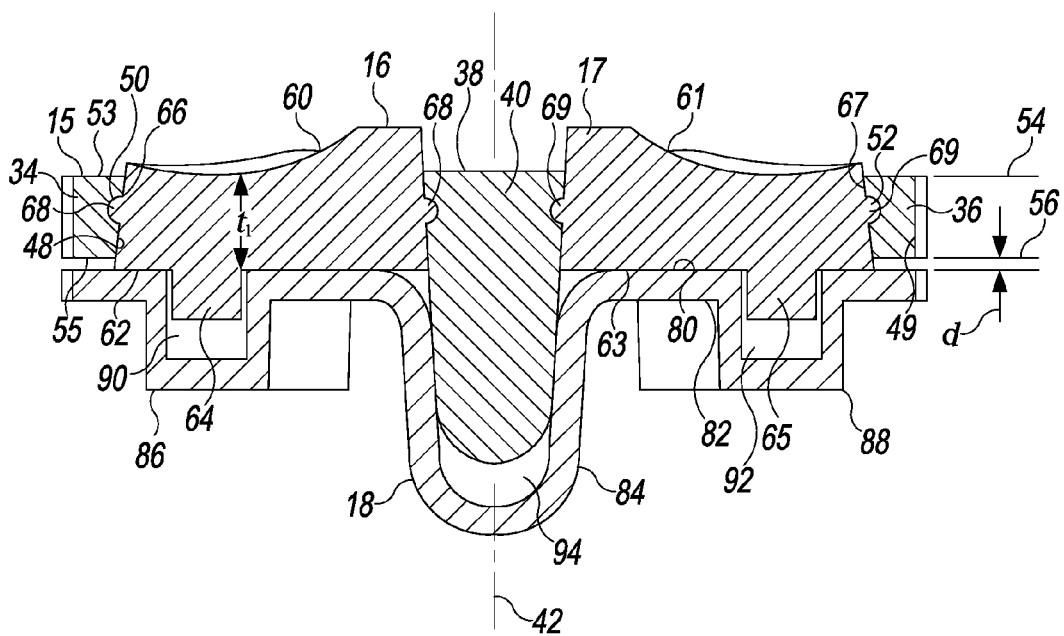
FIG. 4 is a cross-section of the tibial component of FIG. 3, taken along line 4-4 of FIG. 3.
Figure 5:
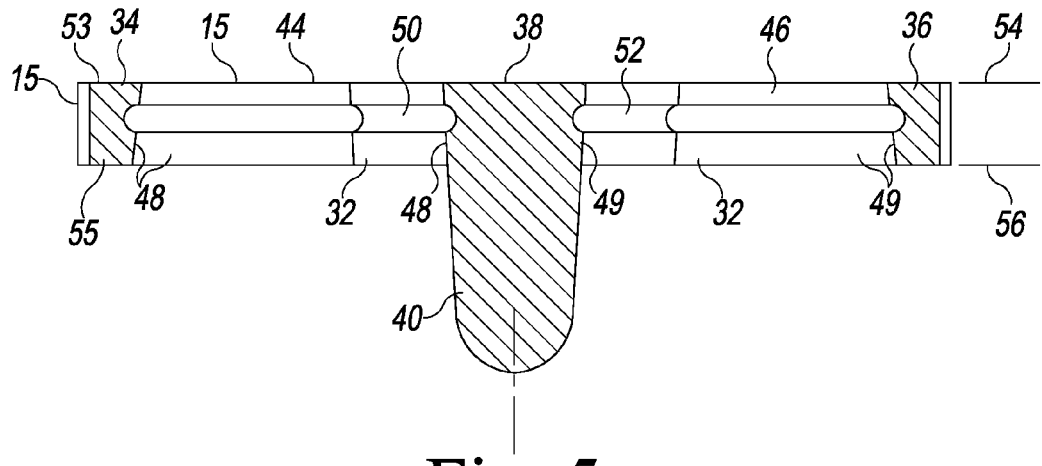
FIG. 5 is a cross-section similar to FIG. 4, showing only the tibial frame of the tibial component of FIGS. 1-4.
Figure 6:
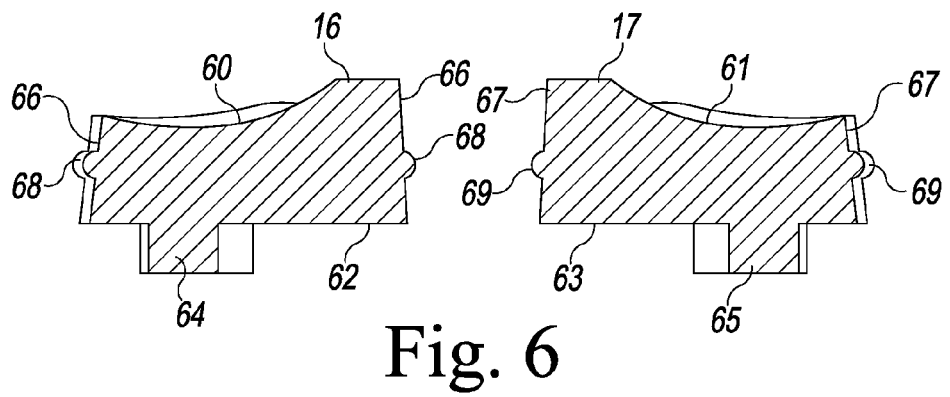
FIG. 6 is cross-section similar to FIG. 4, showing only the medial and lateral bearing components of the tibial component of FIGS. 1-4.
Figure 7:
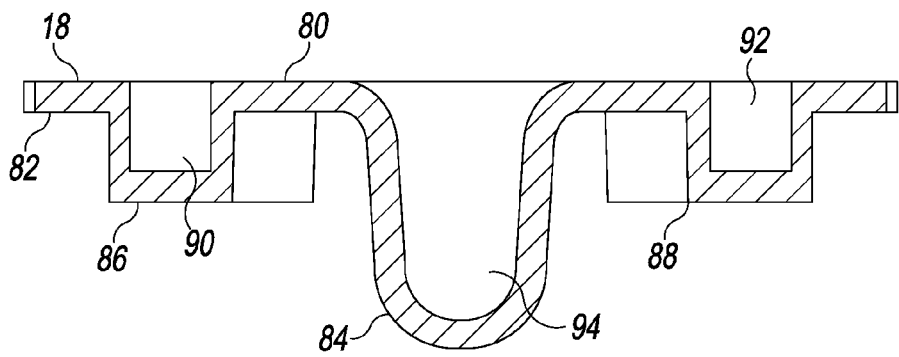
FIG. 7 is cross-section similar to FIG. 4, showing only the tibial base plate of the tibial component of FIGS. 2-4.
Figure 8:
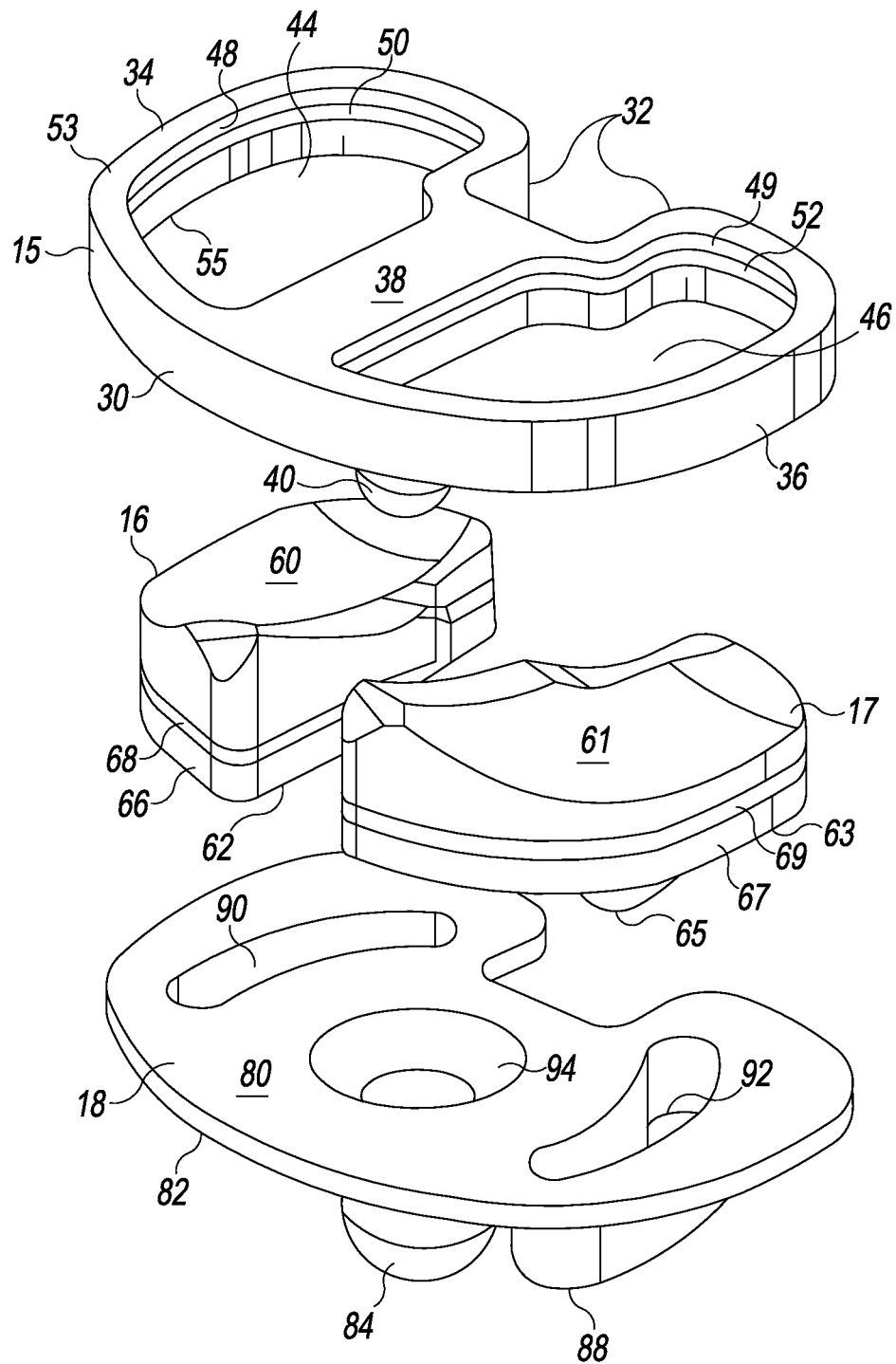
FIG. 8 is an exploded perspective view of the tibial component of FIG. 2.

As shown in FIGS. 4-5, the anterior portion 30, posterior portion 32, medial portion 34 and central portion 38 of the frame 15 have side walls 48 facing the medial opening 44 and the anterior portion 30, posterior portion 32, lateral portion 36 and central portion 38 have side walls 49 facing the lateral opening 46. These side walls 48, 49 have medial and lateral peripheral grooves 50, 52 that face into the medial and lateral openings 44, 46. Each peripheral groove 50, 52 in the illustrated embodiment is continuous, extending around the entire periphery of each opening 44, 46. The peripheral grooves 50, 52 in the illustrated embodiment are generally parallel to and spaced between planes 54, 56 through the proximal and distal surfaces 53, 55 of the tibial frame 15.

The tibial frame 15 may be constructed from a biocompatible metal, such as stainless steel, titanium, cobalt chrome alloy or titanium alloy, although other materials, such as ceramic, may also be used. Alternative materials may be used as well, such as a polymer (polyetherether ketone or PEEK) for example or ceramic.

The medial and lateral openings 44, 46 of the tibial frame 15 receive the medial and lateral bearings 16, 17. These bearings 16, 17 have similar structures, and the description below should be considered to apply to both bearings.

The medial bearing component 16 has a proximal bearing surface 60, a distal surface 62, a peg 64 extending distally from the distal surface 62 and side walls 66 extending between the proximal bearing surface 60 and distal surface 62. The proximal bearing surface 60 is sized and shaped to articulate with the curved articulating surface 19 of the medial condyle of the femoral component 12.

The lateral bearing component 17 including a proximal bearing surface 61, a distal surface 63, a peg 65 extending distally from the distal surface 63 and side walls 67 extending between the proximal bearing surface 61 and distal surface 63. The proximal bearing surface 61 is sized and shaped to articulate with the curved articulating surface 20 of the lateral condyle of the femoral component 12.

In the illustrated embodiment, the curved articulating surfaces defined by the proximal bearing surfaces 60, 61 are concavely curved. It should be understood that other shapes may be used. It should also be understood that the shapes of the medial and lateral articulating surfaces may be different. For example, one articulating surface could have a greater curvature than the other; illustratively, one articulating surface could be curved to substantially match the curvature of the articulating surface of the corresponding femoral component condyle and the other articulating surface could be flat, convex or only slightly concavely curved to not match the curvature of the articulating surface of the corresponding femoral component condyle; in other words, the conformity of the articulating surfaces may differ on the medial and lateral sides to allow for internal and external rotation of the femoral component on the tibial bearings.

The bearing components 16, 17 are sized and shaped to fit within the medial and lateral openings 44, 46 in the tibial frame 15. When assembled, the side walls 48, 49, 66, 67 of the frame 15 and bearings 16, 17 are juxtaposed, with substantially no gap between the side walls 48, 49 of the frame 15 and the side walls 66, 67 of the bearing components 16, 17.

The side walls 66, 67 of the illustrated medial and lateral bearing components 16, 17 include peripheral flanges 68, 69. The illustrated flanges are between the proximal bearing surfaces 60, 61 and the distal surfaces 62, 63 and extend around the entire periphery of each bearing component 16, 17. The illustrated flanges 68, 69 are parallel to the planar distal surfaces 62, 63 of the bearing components 16, 17.

Together the flanges 68, 69 and the peripheral grooves 50, 52 define complementary locking members to selectively lock the medial bearing component 16 in the medial opening 44 of the tibial frame 15 and the lateral bearing component 17 in the lateral opening 46 of the tibial frame 15 when the components 15, 16, 17 are assembled. Thus, the frame 15 and the bearing components 16, 17 can be assembled with the medial bearing component 16 received within the medial opening 44 and the complementary locking members 50, 68 locking together to selectively fix the medial bearing component to the frame 15. Similarly, the frame 15 and the bearing components 16, 17 can be assembled with the lateral bearing component 17 received within the lateral opening 46 and the complementary locking members 52, 69 locking together to selectively fix the lateral bearing component 17 to the frame 15. The complementary locking members 50, 52, 68, 69 may be sized and shaped for a snap-fit. It should be understood that the illustrated complementary locking members are provided as examples only; other locking members could be used, and the invention is not limited to any particular locking mechanism unless expressly called for in the claims.

The bearings 16, 17 may be made of a polymeric material. Suitable polymeric materials for the bearings 16, 17 include ultrahigh molecular weight polyethylene (UHMWPE). The UHMWPE may comprise a cross-linked material, for example. Techniques for crosslinking, quenching, or otherwise preparing UHMWPE are described in numerous issued U.S. patents, examples of which include: U.S. Pat. No. 5,728,748 (and its counterparts) issued to Sun, et al.; U.S. Pat. No. 5,879,400 issued to Merrill et al.; U.S. Pat. No. 6,017,975 issued to Saum, et al.; U.S. Pat. No. 6,242,507 issued to Saum et al.; U.S. Pat. No. 6,316,158 issued to Saum et al.; U.S. Pat. No. 6,228,900 issued to Shen et al.; U.S. Pat. No. 6,245,276 issued to McNulty et al.; and U.S. Pat. No. 6,281,264 issued to Salovey et al. The disclosure of each of these U.S. patents is incorporated by reference herein in their entireties. The UHMWPE of the bearing material may be treated to stabilize any free radicals present therein, such as through the addition of an antioxidant such as vitamin E. Techniques for stabilizing UHMWPE with antioxidants are disclosed, for example, in U.S. Pat. Pub. No. 20070293647A1 (Ser. No. 11/805,867) and U.S. Pat. Pub. No. 20030212161A1 (Ser. No. 10/258,762), both entitled "Oxidation-Resistant And Wear-Resistant Polyethylenes For Human Joint Replacements And Methods For Making Them," the disclosures of which are incorporated herein in their entireties. It should be understood that the present invention is not limited to any particular UHMWPE material or to UHMWPE material for the bearing components 16, 17 unless expressly called for in the claims. It is expected that other materials for the bearings 16, 17 are or will become available that will be useful in applying the principles of the present invention.

Figure 9:
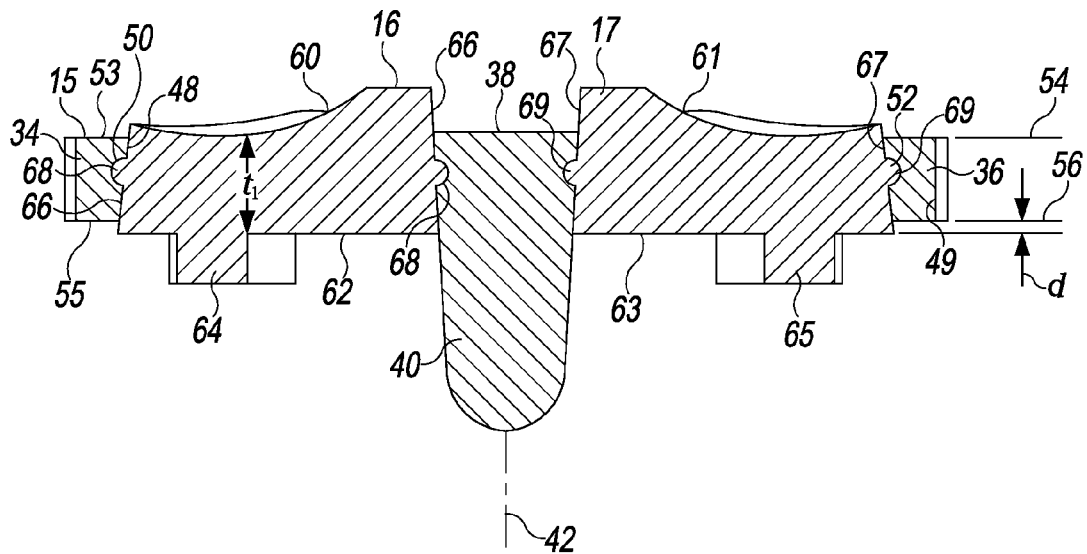
FIG. 9 is a cross-section similar to FIG. 4, showing only an assembly of the tibial frame and tibial bearing components of the tibial component of FIGS. 1-4.

As shown illustratively in FIGS. 4 and 9, when the bearing components 16, 17 and tibial frame 15 are assembled, the distal surfaces 62, 63 and pegs 64, 65 of the bearing components 16, 17 extend distally beyond the distal plane 56 of the tibial frame 15. In the embodiment of FIGS. 4 and 9, the distal surfaces 62, 63 of the two bearing components 16, 17 lie in a common plane 70 that is parallel to the distal plane 56 of the tibial frame 15, and spaced from that plane 56 by a distance shown at "d" in FIGS. 4 and 9. When implanted on the resected tibial plateau (not shown), the distal surfaces 62, 63 of the bearing components 16, 17 will rest directly against the resected proximal tibial surface and the distal surface 55 of the tibial frame 15 will be slightly spaced above the resected proximal tibial surface by the distance "d". When used with the tibial base plate 18 for a rotating platform system, the distal surfaces 62, 63 of the bearing components 16, 17 will rest directly on the proximal surface 80 of the base plate 18, and the distal surface 55 of the tibial frame 15 will be spaced above the proximal surface 80 of the base plate 18 by the distance "d" to avoid these surfaces 55, 80 rubbing against each other as the frame 15 and bearings 16, 17 rotate on the plate 18.

Figure 11:
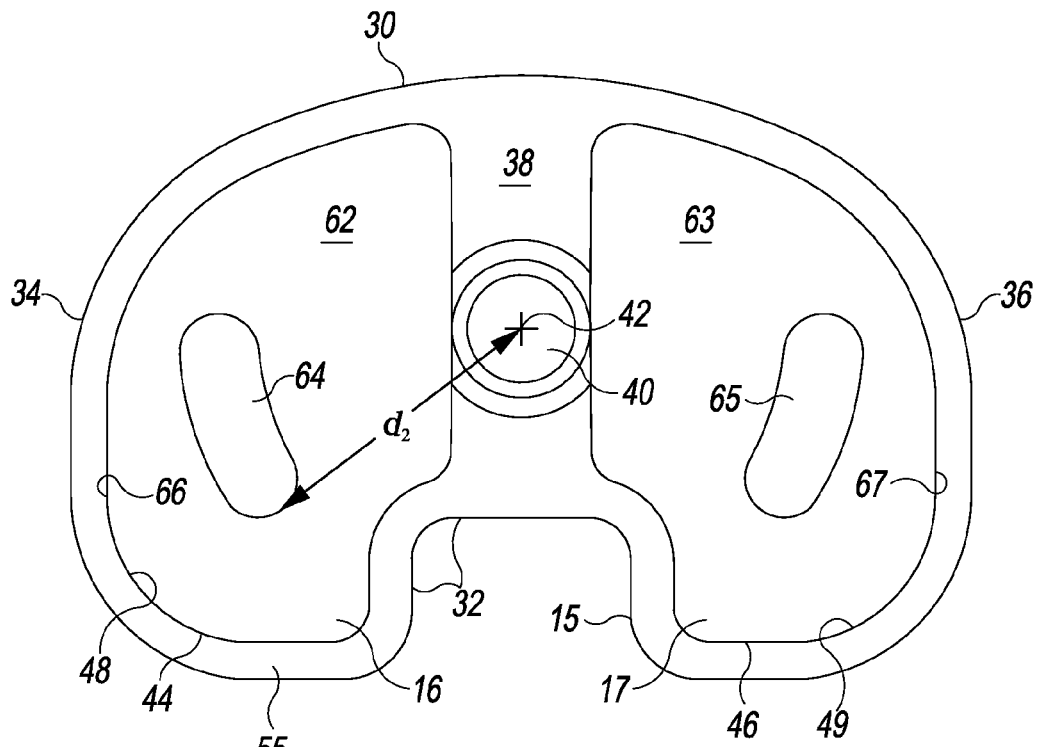
FIG. 11 is a bottom view of the assembly of the tibial frame and bearing components of the fixed bearing tibial component of FIG. 1.

As shown in FIG. 11, the illustrated pegs 64, 65 each have a slightly curved, elongated shape, with their concave surfaces facing inwardly. For the fixed bearing embodiment of FIG. 1, the pegs 64, 65 are designed to be received within openings created in the resected proximal tibial surface. The openings in the resected proximal tibial surface may be substantially complementary in size and shape to the pegs 64, 65, with room for bone cement to be received within the openings as well to fix the assembled tibial component 14 to the tibia.

The tibial component 14 is also secured to the tibia by the stem 40 of the tibial frame 15. When implanted, the stem 40 is received in a recess or opening formed in the resected proximal tibial surface, with bone cement received in the opening to fix the stem 40 to the tibia. If desired, the outer surface of the stem 40 may have cement pockets or other structures to help fix the stem within the opening.

Accordingly, the stem 40 and the pegs 64, 65 should be sized and shaped to fill this function of securing the tibial component 14 to the tibia with no relative rotation between the tibial component 14 and the tibia.

Although described above for cemented fixation, it should be understood that the present invention may be used in cementless applications as well.

The same above-described assembly of the tibial frame 15 and bearing components 16, 17 can be used for a mobile-bearing application by using the assembly of FIG. 1 together with the tibial base plate 18 shown in FIG. 2.

The tibial base plate 18 has a proximal surface 80, a distal surface 82 and a stem 84 extending distally from the distal surface 82. The base plate 18 also has a curved medial keel 86 extending distally from the distal surface 82, a curved lateral keel 88 extending distally from the distal surface 82, a curved medial receptacle 90 in the proximal surface 80 corresponding in shape and position with and extending into the curved medial keel 86, a curved lateral receptacle 92 in the proximal surface 80 corresponding in shape and position with and extending into the curved lateral keel 88 and a central receptacle 94 in the proximal surface 80 extending into the stem 84.

The proximal and distal surfaces 80, 82 of the tibial base plate 18 are substantially planar and parallel to each other. The medial and lateral receptacles 90, 92 are sized and shaped to receive the pegs 64, 65 of the medial and lateral bearing components 16, 17 and are curved to provide a rotational path for the pegs 64, 65. The arc lengths of the medial and lateral receptacles 90, 92 are great enough to allow the pegs 64, 65 to travel along curved paths defined by the receptacles 90, 92. The central receptacle 94 is sized and shaped to receive the stem 40 of the tibial frame 15 and to allow for rotation of the tibial frame about the axis 42 of the stem when the stem 40 is received within the central receptacle 94. Thus, when mounted with the stem 40 received within the central receptacle 94 and the pegs 64, 65 received within their respective receptacles 90, 92, the assembly of the tibial frame 15 and bearing components 16, 17 can rotate about the axis 42 on the base plate 18 to a predetermined extent defined by the arc lengths of the medial and lateral receptacles 90, 92.

An assembly of the tibial base plate 18 with the assembly of the frame 15 and bearing components 16, 17 is illustrated in cross-section in FIG. 4. As there shown, the distal surfaces 62, 63 of the medial and lateral bearing components 16, 17 rest on the proximal surface 80 of the tibial base plate while the distal plane 56 of the distal surface 55 of the frame 15 is spaced above the proximal surface 80 of the base plate by the distance "d". Thus, there should be no rubbing contact between the distal surface 55 of the frame 15 and the proximal surface 80 of the base plate component 18.

The tibial base component 18 may be constructed from a biocompatible metal, such as stainless steel, titanium, cobalt chrome alloy or titanium alloy, although other materials, such as ceramic, may also be used. Alternative materials may be used as well, such as a polymer (polyetherether ketone or PEEK) for example or ceramic.

To accommodate the needs and anatomies of a variety of patients, the components of the present invention may be provided in a kit providing the surgeon with various sizes and options to select from in treating the individual patient. A typical kit may include one or more sizes of tibial frames 15, one or more sizes of bearing components 16, 17 and one or more sizes of tibial base plates 18. Such a kit provides the surgeon the option of determining intraoperatively whether to treat the patient with a fixed bearing knee prosthesis such as illustrated in FIG. 1 or a mobile bearing knee prosthesis such as illustrated in FIG. 2.

Figure 10:
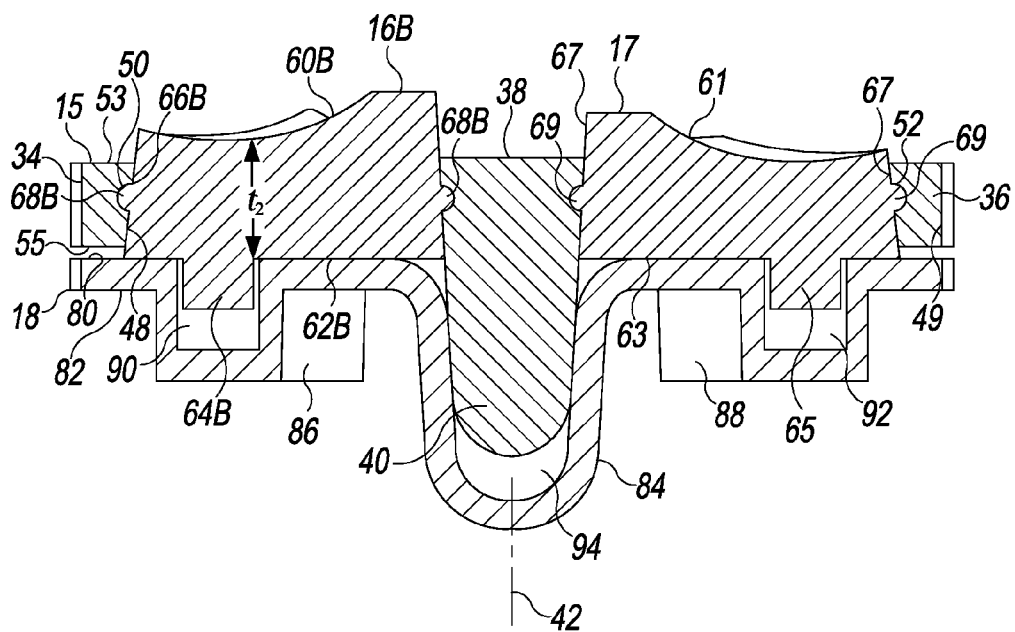
FIG. 10 is cross-section similar to FIG. 4, showing the assembly with two different thicknesses of bearing components.

The surgeon can also be provided with multiple bearing components 16, 17 having medial-lateral and anterior-posterior dimensions to fit within a single size frame 15 but with different thicknesses. Considering FIGS. 4 and 9-10, one medial bearing component 16 may have a minimum thickness shown at "$t_1$" between the proximal bearing surface 60 and the distal surface 62 and a second medial bearing component in the kit, shown at 16B in FIG. 10, may have a greater minimum thickness "$t_2$" between the proximal bearing surface 60B and the distal surface 62B. Similar options can be provided for different thicknesses of lateral bearing components 17. Thus, the surgeon has the flexibility to select the optimum thickness for the two bearings 16, 17 intraoperatively to ensure appropriate tension in the ligaments of the knee. The surgeon also has the flexibility to chose bearing components having different thicknesses for the medial and lateral sides; as shown in FIG. 9, the surgeon may opt to provide a thicker bearing component on the medial side than on the lateral side to place the knee in a slightly varus configuration if desired. Alternatively, the surgeon could opt to provide a thicker bearing component on the lateral side than on the medial side.

In addition, multiple bearing components having the same medial-lateral and anterior-posterior dimensions to fit within one size of tibial frame could be provided, where medial and lateral bearing components having the same size could have differently shaped articulation surfaces. For example, medial and lateral bearing components sized to fit within a single size of tibial frame could have articulation surfaces shaped to optimally articulate with different sizes of femoral components, thereby allowing for optimization of component sizing for both the femur and tibia while maintaining optimal articulation.

The prosthesis kit may also include different sizes of tibial frames 15, bearing components 16, 17 and tibial base plates 18 having different medial-lateral and anterior-posterior dimensions to best fit the patient's anatomy. In the following description, the same reference numbers are used for like portions or elements of the different sizes of components, followed by a letter designation, such as "A" to differentiate the sizes. It should be understood that the above descriptions of the components apply to differently sized components unless expressly distinguished.

Figure 12:
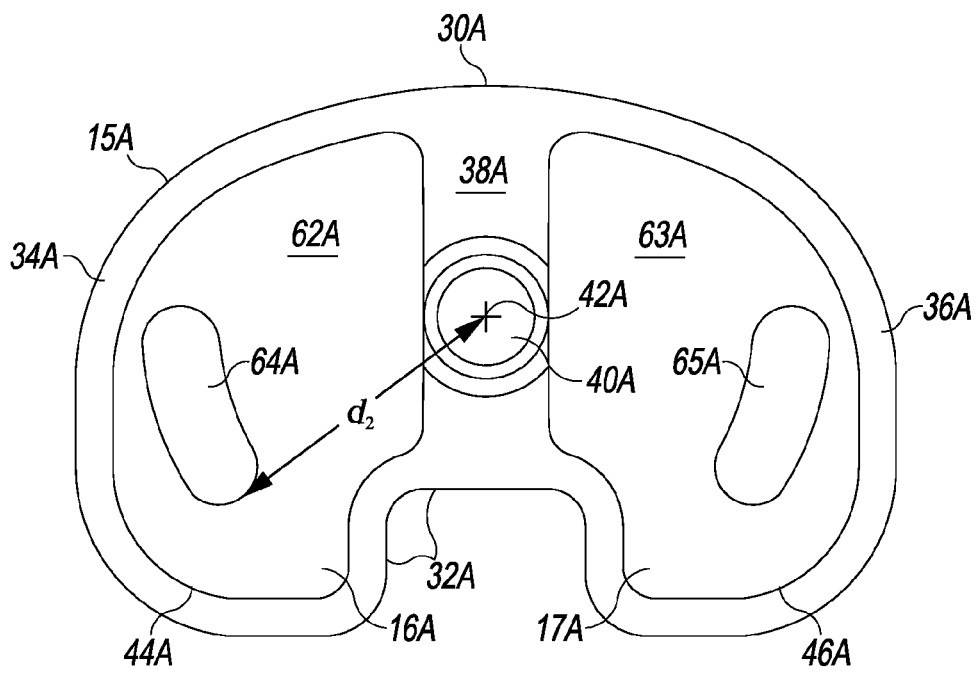
FIG. 12 a bottom view similar to FIG. 11 but showing a smaller size of tibial frame and smaller sizes of bearing components.

FIGS. 11 and 12 illustrate two sizes of tibial frames 15, 15A with medial and lateral bearing components 16, 16A, 17, 17A sized to mate with the size of medial and lateral openings 44, 44A, 46, 46A of the tibial frames 15, 15A. Although the medial-lateral and anterior-posterior dimensions of the bearing components 16, 16A, 17, 17A differ, the pegs 64, 64A, 65, 65A have the same size and shape in the two sizes. Moreover, the distance from the central longitudinal axis 42 of the stem 40 of the first frame 15 to various points on the peg 64 of the first medial bearing component 16 is the same as the distance from the central longitudinal axis 42A of the stem 40A of the second frame 15A to corresponding points on the peg 64A of the second medial bearing component 16A when the medial bearing components 16, 16A are assembled with the frames 15, 15A. This relationship is shown in FIGS. 11 and 12 by the distances marked "$d_2$". The same relationship holds true for the first and second lateral bearing components 17, 17A. Thus, the surgeon can prepare the tibia by resecting the proximal surface and then creating grooves in the medial and lateral sides of the resected surface to receive the pegs. If the surgeon determines that a larger size frame 15 such as that shown in FIG. 11 is best for that patient, the pegs 64, 65 of the larger size frame will fit in the prepared grooves. If the surgeon determines intraoperatively (after the grooves have been formed) that a smaller size frame 15A such as that shown in FIG. 12 is best for that patient, the pegs 64A, 65A of the smaller size frame 15A will fit in the same grooves in the tibia; the surgeon does not have to determine the optimum size of frame before preparing the tibia, but can use the same prepared surface for multiple sizes of frames and bearing components.

Figure 13:
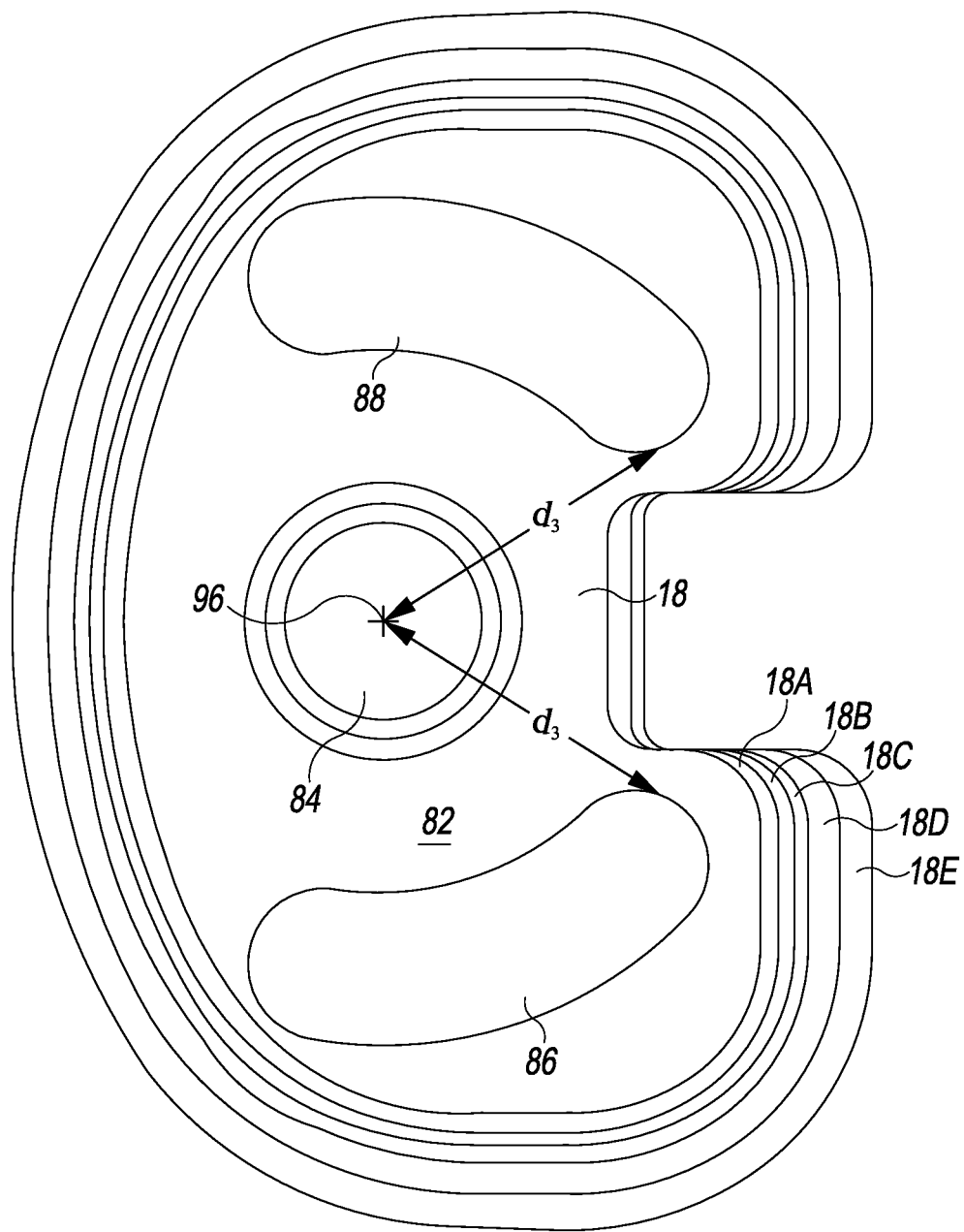
FIG. 13 is a bottom view of the tibial base plate, showing the outlines of multiple sizes of tibial base plates superimposed to illustrate the common size, shape and position of the keels of the tibial base plates.

The same advantage is available with the mobile bearing option. FIG. 13 illustrates the peripheral outlines of multiple sizes of tibial base plates superimposed, the sizes being identified by reference numbers 18, 18A, 18B, 18C, 18D and 18E. Although the medial-lateral and anterior-posterior dimensions of the tibial base plates 18, 18A, 18B, 18C, 18D and 18E differ, the medial and lateral keels 86, 88 have the same size and shape in all sizes. Moreover, the distances from the central longitudinal axis 96 of the stem 84 of the first tibial base plate 18 to various corresponding points on the medial and lateral keels 86, 88 is the same across the various sizes. This relationship is shown in FIG. 13 by the distances marked "$d_3$". Thus, the surgeon can prepare the tibia by resecting the proximal surface and then creating grooves in the medial and lateral sides of the resected surface to receive the medial and lateral keels 86, 88. If the surgeon determines that a larger size such as that shown at 18A in FIG. 13 is best for that patient, the medial and lateral keels of that size tray base will fit in the prepared grooves. If the surgeon determines intraoperatively (after the grooves have been formed) that a smaller size such as that shown at 18 in FIG. 13 is best for that patient, the keels 86, 88 will fit in the same grooves in the tibia; the surgeon does not have to determine the optimum size before preparing the tibia, but can use the same prepared surface for multiple sizes of tibial bases 18, 18A, 18B, 18C, 18D and 18E.

In addition, the present invention allows the surgeon intra-operative flexibility in selecting either a fixed or mobile bearing prosthesis for the patient. For example, if the surgeon plans to use a mobile bearing design utilizing the base plate 18 along with the frame and bearing component assembly, the surgeon can prepare the tibia with grooves positioned, sized and shaped to receive the keels 86, 88 of the tibial base plate 18. If after the grooves have been formed the surgeon determines that a fixed bearing design would be more suitable for the patient, the frame and bearing assembly shown in FIGS. 1 and 9 can be used; the pegs 64, 65 will fit within the grooves prepared to receive the keels 86, 88 and the extra space (due to the smaller size of the pegs 64, 65 compared to the keels 86, 88) can be filled with bone cement. Similarly, if the surgeon initially plans to use a fixed bearing system, prepares the tibia with grooves to receive the pegs 64, 65 and then determines that a mobile bearing system is more suitable for the patient, the surgeon can easily expand the grooves formed in the tibia to receive the keels 86, 88 of the tibial base plate.

In use, the surgeon may follow standard practices in exposing the knee joint and in resecting the distal femur to receive the femoral implant component 12. The surgeon may set the location and orientation of the plane of the proximal tibial resection using standard instruments and procedures. If the surgeon plans to use the fixed bearing knee prosthesis of FIG. 1, the surgeon should be able to preserve additional bone since the bearing components 16, 17 will be placed directly on the resected tibial plateau; the implant assembly will not have the additional thickness associated with the thickness of a tibial plate between the bearing components and the bone.

The surgeon can then use standard surgical instruments in preparing a central opening in the tibia to receive the stem 40 or stem 84. To create the grooves to receive the pegs 64, 65 or keels 86, 88, the instrument set may include, for example, templates with openings sized and shaped to correspond with the sizes and shapes of the pegs 64, 65 and keels 86, 88 so that the surgeon may, for example, use a surgical burr to create the grooves.

Figure 14:
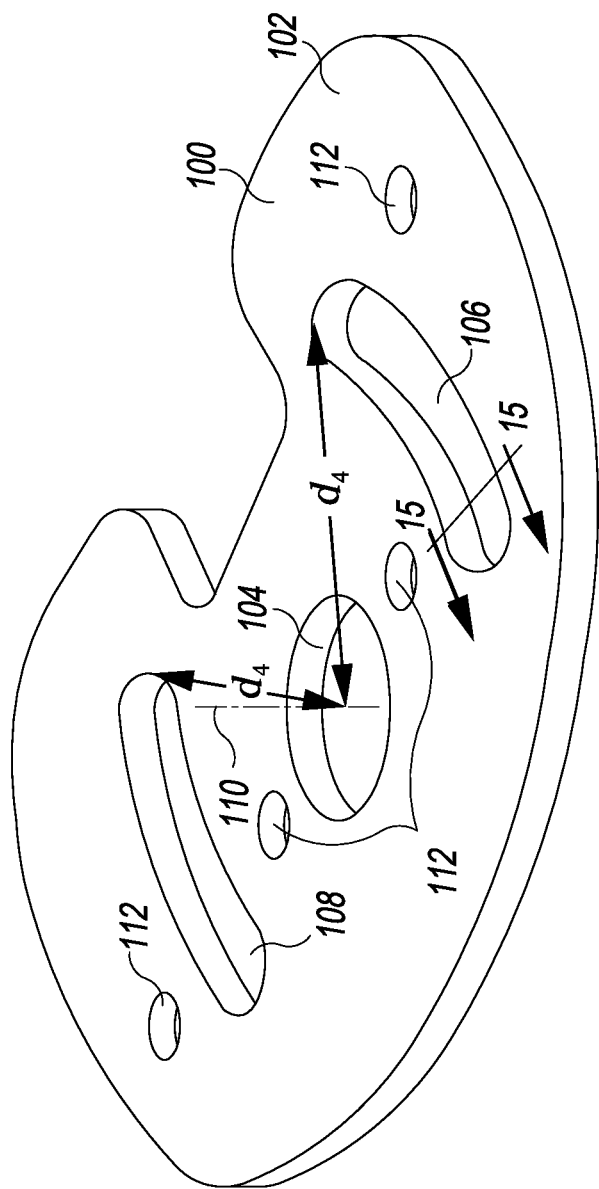
FIG. 14 is a perspective view of a template that may be used to prepare the tibia to receive the illustrated tibial base plates and tibial frames.

An example of a suitable template is illustrated in FIG. 14 at 100. The illustrated template 100 comprises a plate 102 having a round central opening 104 and medial and lateral curved openings 106, 108 spaced from the central opening 104. The central opening 104 has a central longitudinal axis 110; the distances from the central longitudinal axis 110 of the central opening 104 of the template 100 to corresponding points on the medial and lateral curved openings is illustrated in FIG. 14 by the distances marked "$d_4$". The distance $d_4$ corresponds with the distances $d_3$ for multiple sizes of tibial base plates, such as tibial base plates 18, 18A and 18B, and the sizes and shapes of the medial and lateral curved openings 106, 108 correspond with the sizes and shapes of the medial and lateral keels 86, 88 of multiple sizes of tibial base plates. The diameter of the round central opening 104 corresponds with the diameters of the stem 84 of one or more sizes of tibial base plates. It should be understood that a surgical kit may include multiple sizes of templates 100, if not all sizes tibial base plates share keels having the same size, shape and position.

Figure 16:
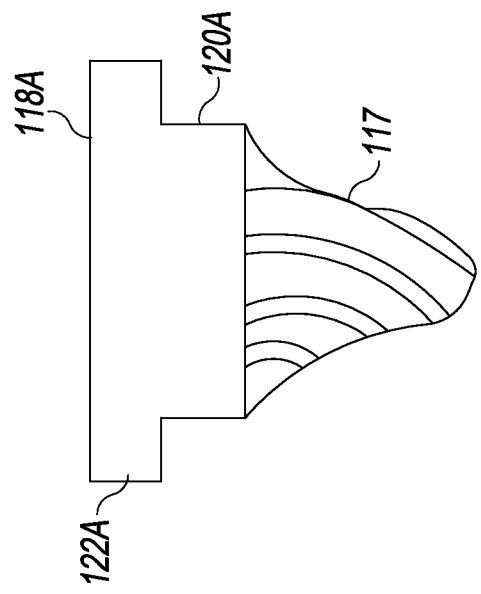
FIG. 16 is a front view of one type of bit or reamer that may be used with the template of FIG. 14 to create the central conical bore to receive the stem of either the tibial frame or the tibial base plate.
Figure 15:
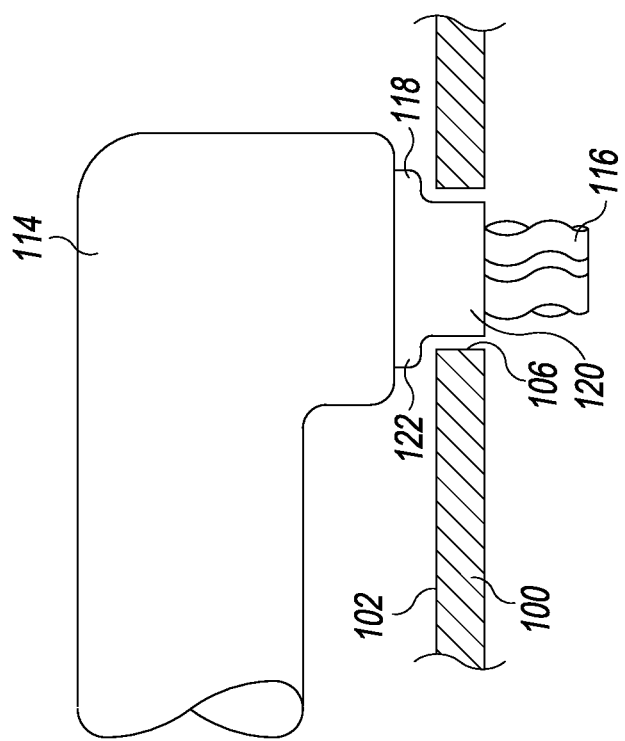
FIG. 15 is a diagrammatic illustration of a drill and one type of bit in use with the template of FIG. 14 to create one of the medial and lateral grooves, with a portion of the tibial base plate being shown in cross-section (along line 15-15 of FIG. 14)

The surgeon can prepare the tibia by resecting the proximal surface and then placing the template 100 on the resected tibial surface. The illustrated template 100 includes a plurality of spaced holes 112 to receive Steinmann pins (not shown) to temporarily secure the template to the tibia. To prepare the slots and tapered opening to receive the keels 86, 88 and stem 84 of the tibial base plate, the surgeon may use, for example, a 90 degree or right angle drill, shown in FIG. 15 at 114 with a milling bit or burr 116 and a tapered milling bit or reamer, shown at 117 in FIG. 16. Both bits 116, 117 have depth controlling housings 118, 118A. In the illustrated embodiments, the depth-controlling housings 118, 118A includes a first cylindrical portion 120, 120A having diameters sized to fit within the medial and lateral openings 106, 108 and central opening 104 and to be guided by the walls of the template 100 defining these openings 104, 106, 108. The first cylindrical portions 120, 120A have axial lengths generally corresponding with the thickness of the template plate 102. Each housing 118, 118A also has enlarged diameter portions 122, 122A with surfaces that rest on the surface of the template plate 102 to control the depths of the grooves and bore to be created.

Using the illustrated template 100 and bits 116, 117, the surgeon can prepare curved medial and lateral grooves and a conical central opening of controlled shape, position and depth, all sized and shaped to receive multiple sizes of tibial base plates (for example, tibial base plates 18, 18A, 18B, 18C, 18D, 18E). If the surgeon determines intraoperatively to use a fixed bearing prosthesis, the surgeon can use the grooves created for the keels 86, 88 to instead receive the pegs 64, 65 (and use bone cement to fill in any gap in the grooves between the pegs and the walls of the grooves).

During trialing, the surgeon may determine the optimum size of tibial frame 15 (and base plate 18 if used) for the particular patient's tibia. This decision may be made independently of the size of the femoral component. Moreover, since the pegs 64, 65 and keels 86, 88 are commonly sized and shaped for multiple sizes of frames 15 and base plates 18, the surgeon can select the optimum size implant component without performing any additional bone preparation.

The surgeon may then select the bearing components 16, 17 from the kit that provide the optimum articulation surface for the size of femoral component and the optimum tension in the ligaments. Since the thicknesses of the bearing components 16, 17 do not need to match, the surgeon can select a thicker bearing component for either the medial or lateral side to, for example, provide a varus alignment of the leg. Alternatively, the bearing component thicknesses can be selected to ensure alignment along the mechanical axis of the leg. Once the bearing components are selected, the surgeon can quickly and easily snap them into their respective openings 44, 46 in the frame 15, with the flanges 68, 69 received in the peripheral grooves 50, 52 in the side walls 48, 49 of the frame 15.

Thus, the present invention provides a knee prosthesis system that allows the surgeon to preserve healthy tibial bone stock and that allows for intraoperative flexibility in selecting the appropriate size and type (fixed or mobile) of components after the bone surface has been prepared.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

We claim:

1. A knee prosthesis system comprising:
   a femoral component having medial and lateral condyles with curved articulating surfaces;
   a tibial component comprising a first frame having an anterior portion, a posterior portion, a medial portion extending between the anterior portion and the posterior portion, a lateral portion extending between the anterior portion and the posterior portion, a central portion extending between the anterior portion and the posterior portion, a stem extending distally from the central portion, the stem having a central longitudinal axis and an outer surface tapering distally toward the central longitudinal axis;
   the anterior portion, posterior portion, medial portion, lateral portion and central portion defining spaced first medial and first lateral openings, the first medial opening extending from the medial portion of the first frame to the central portion of the first frame and the first lateral opening extending from the lateral portion of the first frame to the central portion of the first frame,
   the anterior portion, posterior portion, medial portion and central portion having side walls facing the medial opening;
   the anterior portion, posterior portion, lateral portion and central portion having side walls facing the lateral opening;
   a first medial bearing component including a proximal bearing surface, a distal surface, a peg extending distally from the distal surface and side walls extending between the proximal bearing surface and distal surface, the proximal bearing surface being sized and shaped to articulate with the curved articulating surface of the medial condyle of the femoral component;
   a first lateral bearing component including a proximal bearing surface, a distal surface, a peg extending distally from the distal surface and side walls extending between the proximal bearing surface and distal surface, the proximal bearing surface being sized and shaped to articulate with the curved articulating surface of the lateral condyle of the femoral component;
   the first medial bearing component being sized and shaped to fit within the first medial opening in the first frame with the side walls of the first medial bearing component juxtaposed with the side walls of the first frame facing the first medial opening;
   the first lateral bearing component being sized and shaped to fit within the first lateral opening in the first frame with the side walls of the first lateral bearing component juxtaposed with the side walls of the first frame facing the first lateral opening; and
   the side walls of the first medial bearing component, first lateral bearing component and first frame having complementary locking members to selectively lock the first medial bearing component in the first medial opening and the first lateral bearing component in the first lateral opening;
   wherein the first frame and first medial bearing component and first lateral bearing component can be assembled with the first medial bearing component received within the first medial opening so that the side walls of the first medial bearing component and side walls of the first frame surrounding the medial opening lock together to selectively fix the first medial bearing component to the first frame and so that the side walls of the first lateral bearing component and side walls of the first frame surrounding the first lateral opening lock together to selectively fix the first lateral bearing component to the first frame.

2. The knee prosthesis system of claim 1 wherein:
   the first medial bearing component has a minimum thickness between the proximal bearing surface and the distal surface, the first lateral bearing component has a minimum thickness between the proximal bearing surface and the distal surface and the system further comprises a second medial bearing component and a second lateral bearing component, the second medial bearing component including a proximal bearing surface, a distal surface, a peg extending distally from the distal surface and side walls extending between the proximal bearing surface and distal surface, the proximal bearing surface being sized and shaped to articulate with the curved articulating surface of the medial condyle of the femoral component, the second medial bearing component having a minimum thickness greater than the minimum thickness of the first medial bearing component; and the second lateral bearing component including a proximal bearing surface, a distal surface, a peg extending distally from the distal surface and side walls extending between the proximal bearing surface and distal surface, the proximal bearing surface being sized and shaped to articulate with the curved articulating surface of the lateral condyle of the femoral component, the second lateral bearing component having a minimum thickness greater than the minimum thickness of the first lateral bearing component;

the side walls of the second medial bearing component and second lateral bearing component having locking members complementary to the locking members of the first frame to selectively lock the second medial bearing component in the first medial opening and the second lateral bearing component in the first lateral opening;

wherein the first frame and second medial bearing component and second lateral bearing component can be assembled with the second medial bearing component received within the medial opening so that the side walls of the second medial bearing component and side walls of the first frame surrounding the medial opening lock together to selectively fix the second medial bearing component to the first frame and so that the side walls of the second lateral bearing component and side walls of the first frame surrounding the lateral opening lock together to selectively fix the second lateral bearing component to the first frame.

3. The knee prosthesis system of claim 2 wherein the first frame is assembled with the first medial bearing component locked in place in the first medial opening and the second lateral bearing component locked in place in the first lateral opening.

4. The knee prosthesis system of claim 2 wherein the first frame is assembled with the second medial bearing component locked in place in the first medial opening and the first lateral bearing component locked in place in the first lateral opening.

5. The knee prosthesis system of claim 2 wherein the first frame is assembled with the first medial bearing component locked in place in the first medial opening and the first lateral bearing component locked in place in the first lateral opening.

6. The knee prosthesis system of claim 2 wherein the first frame is assembled with the second medial bearing component locked in place in the first medial opening and the second lateral bearing component locked in place in the first lateral opening.

7. The knee prosthesis system of claim 1 further comprising a tibial base plate including a proximal surface and a distal surface, the tibial base plate having:
a stem extending distally from the distal surface;
a curved medial keel extending distally from the distal surface;
a curved lateral keel extending distally from the distal surface;
a curved medial receptacle in the proximal surface corresponding in shape and position with and extending into the curved medial keel;
a curved lateral receptacle in the proximal surface corresponding in shape and position with and extending into the curved lateral keel; and
a central receptacle in the proximal surface extending into the stem;
wherein an assembly of the first frame and the first medial bearing component and first lateral bearing component is rotatably mountable on the tibial base plate with the stem of the first frame received in the central receptacle and the peg of the medial bearing component received in the curved medial receptacle and the peg of the lateral bearing component received in the curved lateral receptacle;
wherein the pegs and curved medial receptacle and curved lateral receptacle are sized and shaped so that the pegs of the first medial bearing component and first lateral bearing component can travel along curved paths as the first frame and first medial bearing component and first lateral bearing component rotate on the tibial base plate.

8. The knee prosthesis system of claim 1 wherein:
the first frame has a proximal surface and a distal surface;
when assembled with the first frame, the pegs of the first medial and first lateral bearing components extend beyond the level of the distal surface of the frame.

9. The knee prosthesis system of claim 8 wherein:
the distal surface of the first medial bearing component is planar;
the distal surface of the first lateral bearing component is planar; and
when assembled with the first frame, the distal surface of the first medial bearing component extends distally beyond the level of the distal surface of the first frame; and
when assembled with the first frame, the distal surface of the first lateral bearing component extends distally beyond the level of the distal surface of the first frame.

10. The knee prosthesis system of claim 9 wherein:
the distal surface of the first frame lies in a distal plane and includes surfaces of the anterior portion, posterior portion, medial portion and central portion of the first frame; and
the stem is the only part of the first frame that extends distally beyond the distal plane.

11. The knee prosthesis system of claim 10 further comprising a tibial base plate including a proximal surface and a distal surface, the tibial base plate having:
a stem extending distally from the distal surface;
a curved medial keel extending distally from the distal surface;
a curved lateral keel extending distally from the distal surface;
a curved medial receptacle in the proximal surface corresponding in shape and position with and extending into the curved medial keel;
a curved lateral receptacle in the proximal surface corresponding in shape and position with and extending into the curved lateral keel; and
a central receptacle in the proximal surface extending into the stem;
wherein an assembly of the first frame and the first medial bearing component and first lateral bearing component is rotatably mountable on the tibial base plate with the stem of the first frame received in the central receptacle, the peg of the first medial bearing component received in the curved medial receptacle, the peg of the first lateral bearing component received in the curved lateral receptacle, the distal surface of the first medial bearing component contacting the proximal surface of the tibial base plate, the distal surface of the first lateral bearing component contacting the proximal surface of the tibial base plate, and the plane of the distal surface of the tibial frame is spaced from the proximal surface of the tibial base plate;

wherein the pegs and curved medial receptacle and curved lateral receptacle are sized and shaped so that the pegs of the first medial bearing component and first lateral bearing component can travel along curved paths as the first frame and first medial bearing component and first lateral bearing component rotate on the tibial base plate.

12. The knee prosthesis system of claim 1 further comprising:
a second tibial component comprising a second frame, a second medial bearing component and a second lateral bearing component, the second frame having an anterior portion, a posterior portion, a medial portion extending between the anterior portion and the posterior portion, a lateral portion extending between the anterior portion and the posterior portion, a central portion extending from the anterior portion to the posterior portion, and a stem extending distally from the central portion, the stem having a central longitudinal axis and an outer surface tapering distally toward the central longitudinal axis;
the anterior portion, posterior portion, medial portion, lateral portion and central portion defining spaced medial and lateral openings, the medial opening extending from the medial portion of the second frame to the central portion of the frame and the lateral opening extending from the lateral portion of the second frame to the central portion of the second frame,
the anterior portion, medial portion and central portion having side walls facing the medial opening;
the anterior portion, lateral portion and central portion having side walls facing the lateral opening;
wherein:
the first tibial component has a maximum medial-lateral dimension at the medial and lateral portions of the frame and a maximum central anterior-posterior dimension along the central portion;
the second tibial component has a maximum medial-lateral dimension at the medial and lateral portions of the frame and a maximum central anterior-posterior dimension along the central portion;
the maximum medial-lateral dimension of the second tibial component is greater than the maximum medial-lateral dimension of the first tibial component;
the second medial bearing component includes a proximal bearing surface, a distal surface, a peg extending distally from the distal surface and side walls extending between the proximal bearing surface and distal surface, the proximal bearing surface being sized and shaped to articulate with the curved articulating surface of the medial condyle of the second femoral component;
the second lateral bearing component includes a proximal bearing surface, a distal surface, a peg extending distally from the distal surface and side walls extending between the proximal bearing surface and distal surface, the proximal bearing surface being sized and shaped to articulate with the curved articulating surface of the lateral condyle of the second femoral component;
the second medial bearing component is sized and shaped to fit within the medial opening in the second frame with the side walls of the second medial bearing component juxtaposed with the side walls of the frame facing the medial opening;
the second lateral bearing component is sized and shaped to fit within the lateral opening in the second frame with the side walls of the lateral bearing component juxtaposed with the side walls of the second frame facing the lateral opening;
the side walls of the second medial bearing component, second lateral bearing component and second frame having complementary locking members to selectively lock the second medial bearing component in the medial opening and the second lateral bearing component in the lateral opening; and
the second frame and second medial and second lateral bearing components can be assembled with the second medial bearing component received within the second medial opening so that the side walls of the second medial bearing component and side walls of the second frame surrounding the second medial opening lock together to selectively fix the second medial bearing component to the second frame and so that the side walls of the second lateral bearing component and side walls of the second frame surrounding the second lateral opening lock together to selectively fix the second lateral bearing component to the second frame.

13. The knee prosthesis system of claim 12 wherein:
the peg of the first medial bearing component has the same size and shape as the peg of the second medial bearing component;
the peg of the first lateral bearing member has the same size and shape as the peg of the second lateral bearing member;
the distance from the central longitudinal axis of the stem of the first frame to a point on the peg of the first medial bearing component is the same as the distance from the central longitudinal axis of the stem of the second frame to a corresponding point on the peg of the second medial bearing component when the first medial bearing component is assembled with the first frame and the second medial bearing component is assembled with the second frame; and
the distance from the central longitudinal axis of the stem of the first frame to a point on the peg of the first lateral bearing component is the same as the distance from the central longitudinal axis of the stem of the second frame to a corresponding point on the peg of the second lateral bearing component when the first lateral bearing component is assembled with the first frame and the second lateral bearing component is assembled with the second frame.

14. The knee prosthesis system of claim 13 further comprising a first tibial base plate and a second tibial base plate, each tibial base plate including:
a proximal surface;
a distal surface;
a stem extending distally from the distal surface;
a curved medial keel extending distally from the distal surface;
a curved lateral keel extending distally from the distal surface;

a curved medial receptacle in the proximal surface corresponding in shape and position with and extending into the curved medial keel;
a curved lateral receptacle in the proximal surface corresponding in shape and position with and extending into the curved lateral keel; and
a central receptacle in the proximal surface extending into the stem;
wherein:
an assembly of the first frame and the first medial bearing component and first lateral bearing component is rotatably mountable on each tibial base plate with the stem of the first frame received in the central receptacle of the tibial base plate and the peg of the medial bearing component received in the curved medial receptacle and the peg of the lateral bearing component received in the curved lateral receptacle;
wherein the pegs and each curved medial receptacle and curved lateral receptacle are sized and shaped so that the pegs of the first medial bearing component and first lateral bearing component can travel along curved paths as the first frame and first medial bearing component and first lateral bearing component rotate on each tibial base plate;
the distance from the central longitudinal axis of the stem of the first tibial base plate to a point on the medial keel of the first tibial base plate is the same as the distance from the central longitudinal axis of the stem of the second tibial base plate to a corresponding point on the medial keel of the second tibial base plate; and
the distance from the central longitudinal axis of the stem of the first tibial base plate to a point on the lateral keel of the first tibial base plate is the same as the distance from the central longitudinal axis of the stem of the second tibial base plate to a corresponding point on the lateral keel of the second tibial base plate.

15. The knee prosthesis system of claim 14 wherein the first tibial base plate has a maximum medial-lateral dimension and the second tibial base plate has a greater maximum medial-lateral dimension.

* * * * *